(12) United States Patent
Schaeffer

(10) Patent No.: US 7,232,462 B2
(45) Date of Patent: Jun. 19, 2007

(54) SELF CENTERING DELIVERY CATHETER

(75) Inventor: Darin Schaeffer, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 468 days.

(21) Appl. No.: 10/814,988

(22) Filed: Mar. 31, 2004

(65) Prior Publication Data
US 2005/0222604 A1    Oct. 6, 2005

(51) Int. Cl.
A61F 2/01    (2006.01)
A61M 25/00    (2006.01)
A61M 29/00    (2006.01)

(52) U.S. Cl. .................................. 623/11.11; 606/200
(58) Field of Classification Search ...................... None
See application file for complete search history.

(56) References Cited

U.S. PATENT DOCUMENTS

| 3,913,565 A | | 10/1975 | Kawahara |
| 4,619,246 A | | 10/1986 | Molgaard-Nielsen et al. |
| 4,781,682 A | | 11/1988 | Patel |
| 4,878,893 A | | 11/1989 | Chin |
| 5,011,488 A | | 4/1991 | Ginsburg |
| 5,167,239 A | | 12/1992 | Cohen et al. |
| 5,329,942 A | | 7/1994 | Gunther et al. |
| 5,421,832 A | | 6/1995 | Lefebvre |
| 5,840,067 A | | 11/1998 | Berguer et al. |
| 5,846,251 A | | 12/1998 | Hart |
| 5,941,896 A | * | 8/1999 | Kerr .......................... 606/200 |
| 5,971,938 A | | 10/1999 | Hart et al. |
| 6,071,263 A | * | 6/2000 | Kirkman .................... 604/104 |
| 6,179,859 B1 | | 1/2001 | Bates et al. |
| 6,193,739 B1 | * | 2/2001 | Chevillon et al. ........... 606/200 |
| 6,196,966 B1 | | 3/2001 | Kerin et al. |
| 6,210,370 B1 | | 4/2001 | Chi-Sing et al. |
| 6,213,976 B1 | | 4/2001 | Trerotola |
| 6,319,244 B2 | | 11/2001 | Suresh et al. |
| 6,371,971 B1 | * | 4/2002 | Tsugita et al. .............. 606/200 |
| 6,447,530 B1 | * | 9/2002 | Ostrovsky et al. .......... 606/200 |
| 6,447,540 B1 | | 9/2002 | Fontaine et al. |
| 6,558,349 B1 | | 5/2003 | Kirkman |
| 6,569,150 B2 | | 5/2003 | Teague et al. |
| 2002/0161377 A1 | * | 10/2002 | Rabkin ....................... 606/108 |
| 2003/0150821 A1 | | 8/2003 | Bates et al. |
| 2004/0098033 A1 | * | 5/2004 | Leeflang et al. ............ 606/200 |
| 2005/0101982 A1 | * | 5/2005 | Ravenscroft et al. ....... 606/182 |
| 2005/0234503 A1 | * | 10/2005 | Ravenscroft et al. ....... 606/200 |

* cited by examiner

Primary Examiner—Glenn K. Dawson
(74) Attorney, Agent, or Firm—Brinks Hofer Gilson & Lione

(57) ABSTRACT

A self centering delivery catheter is provided for delivering a filter into a vessel in a centered manner which aids in the retrieval of the filter. The delivery catheter generally includes an outer sheath and a cannula disposed inside the outer sheath and axially translatable relative thereto. A set of centering legs are attached to the cannula. The centering legs are operable between a first retracted position and a second extended position, the centering legs moving radially away from the cannula as the centering legs move from the retracted position to the extended position. The relative position of the outer sheath and cannula control the operation of the centering legs. A control wire is disposed inside the cannula and is axially translatable relative thereto. Axial translation of the control wire operates a release mechanism to disengage the filter for delivering the filter into the vessel.

11 Claims, 5 Drawing Sheets

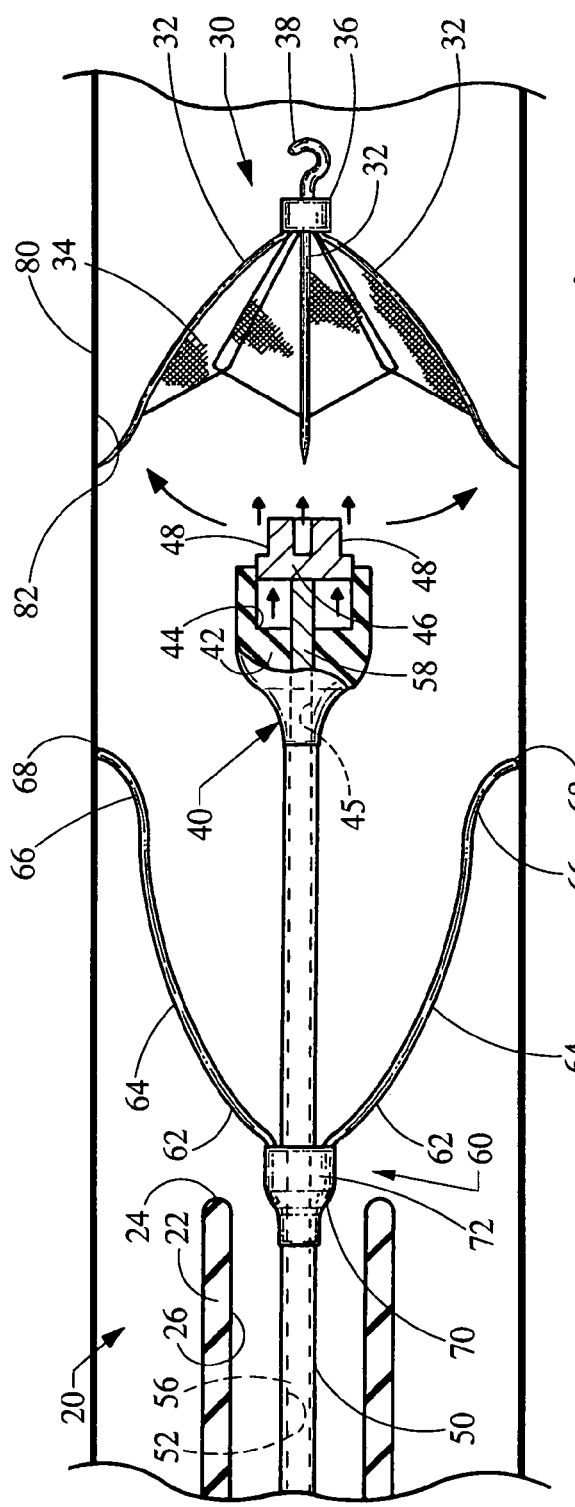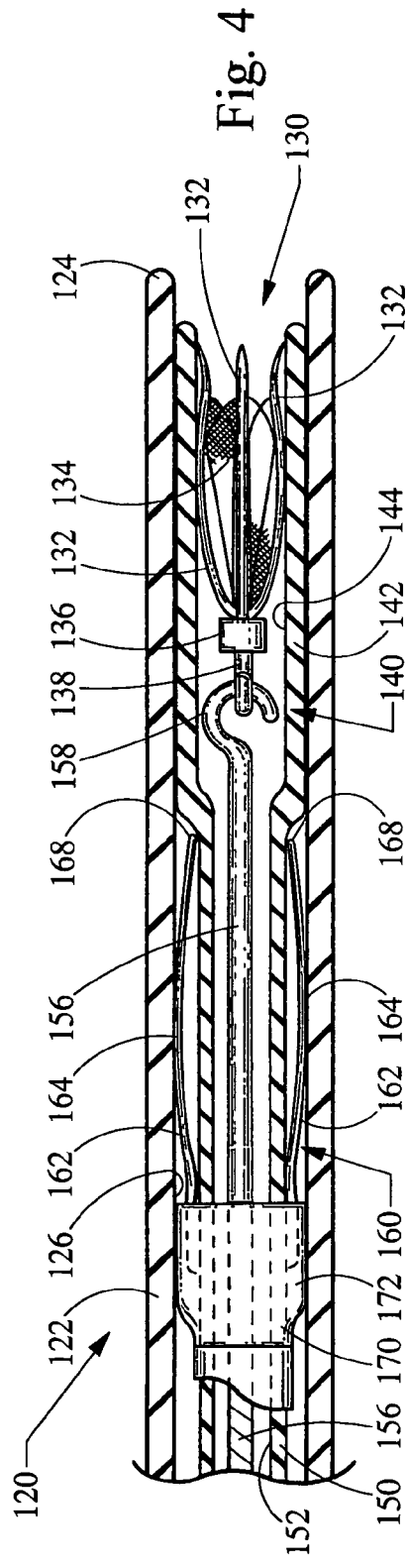

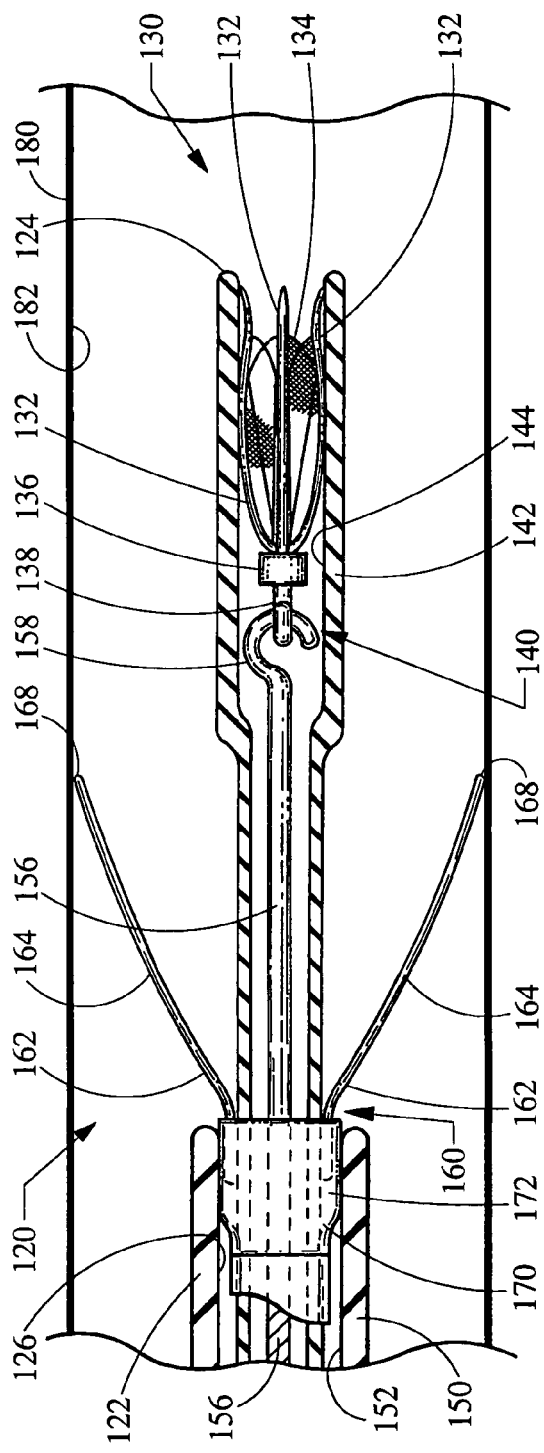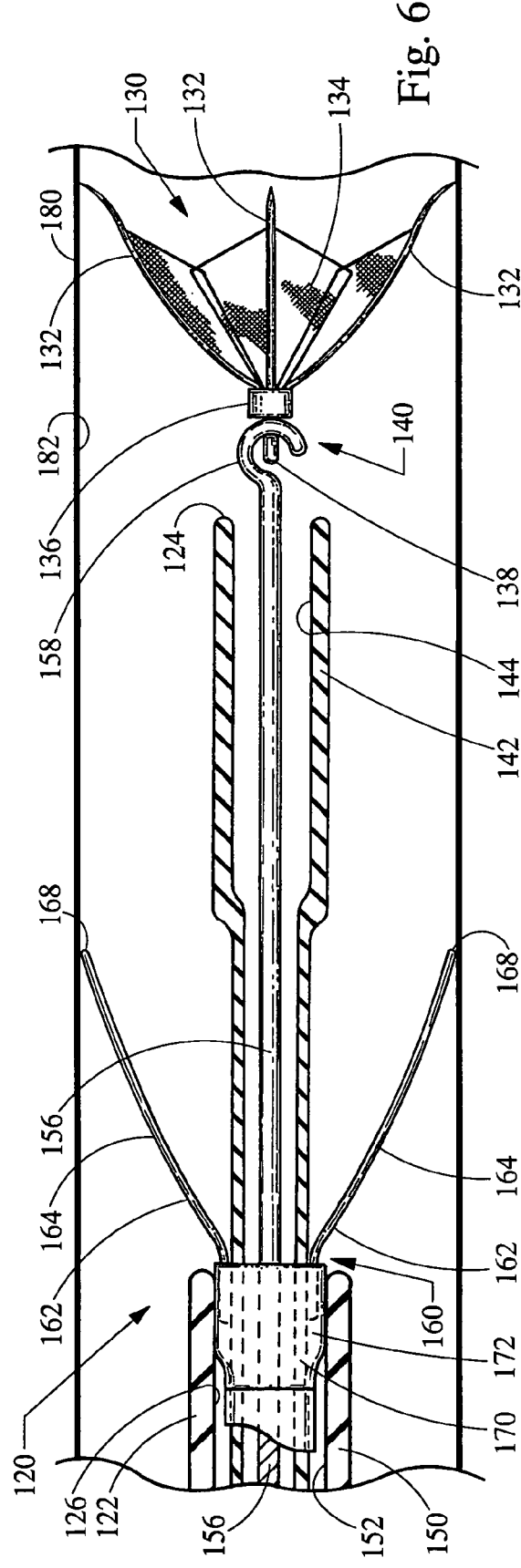

SELF CENTERING DELIVERY CATHETER

FIELD OF THE INVENTION

The present invention relates generally to catheters, and more particularly relates to a delivery catheter for deploying an expandable intraluminal device such as a filter in a vessel.

BACKGROUND OF THE INVENTION

Certain interventional devices, an in particular expandable intraluminal devices such as a retrievable filter, need to be deployed into a vessel for a period of time, after which the filter is retrieved. Such devices typically include a set of struts which are biased outwardly for engagement with the vessel wall. The struts are concentrically spaced about a central axis. A hub is connected to one end of each of the struts such that the filter forms a somewhat conical shape in this deployed state. A retrieval hook extends outwardly from the hub for grasping and retrieving the filter.

Such filters need to be deployed into a vessel as centered as possible. Unfortunately, if the filter tilts, it may be more difficult to retrieve. More specifically, if the central axis of the filter is not aligned with (i.e. skewed from) an axis of the vessel, the biased struts will undesirably press against the vessel wall with different forces. Further, the retrieval hook will be misaligned with the central axis of the vessel, making if difficult for retrieval mechanisms to engage the retrieval hook. Likewise, the offset retrieval hook could block working components of the retrieval mechanism or catheter.

Accordingly, there exists a need to provide an apparatus and method for delivering a filter into a vessel such that the filter is substantially centered within the vessel for aiding in the eventual retrieval of the filter.

BRIEF SUMMARY OF THE INVENTION

One embodiment of the present invention provides a self centering delivery catheter for delivering a filter into a vessel in a centered manner which aids in the retrieval of the filter. The delivery catheter generally comprises an outer sheath and a cannula disposed inside the outer sheath and axially translatable relative thereto. A set of centering legs are attached to the cannula. The centering legs are operable between a first retracted position in a second extended position, the centering legs moving radially away from the cannula as the centering legs move from the first retracted position to the second retracted position. The relative position of the outer sheath and cannula control the operation of the centering legs between the first and second positions. A control wire is disposed inside the cannula and is axially translatable relative thereto. A release mechanism is attached to a distal end of the control wire and is structured to engage and disengage the filter. Axial translation of the control wire operates the release mechanism to disengage the filter for delivering the filter into the vessel.

According to more detailed aspects, the centering legs are biased towards the second extended position. The centering legs are positioned inside the outer sheath in the first retracted position, and are positioned outside the outer sheath in the second extended position. The centering legs are preferably constructed of a memory material. The free end of each center leg is atraumatic. Each centering leg preferably has a concave curvature facing the cannula, and may further include a second curvature facing away from the cannula. That is, a free end of each centering leg may have a curvature extending radially away from the cannula.

The release mechanism may take several forms. In one form, the release mechanism includes a hook formed at the distal end of the control wire for engagement with the retrieval hook and hub of the filter, while the cannula includes a distal end of increased diameter for receiving the filter. In another form, the release mechanism includes a cap formed at a distal end of the cannula. The cap includes a bore receiving a cylinder, the cylinder operatively connected to a distal end of the control wire. The cylinder includes channels receiving struts of the filter, the cap and cylinder cooperating to engage the filter and retain the same. Axial translation of the control wire positions the cylinder relative to the cap to disengage the filter.

Another embodiment of the present invention provides a method for delivering a filter inside a vessel. The method includes the steps of providing a self centering delivery catheter as described above, placing the self centering delivery catheter within the vessel, translating the outer sheath axially relative to the cannula to expose the set of centering legs and allow the set of centering legs to move radially away from the cannula and engage a wall of the vessel, and translating the control wire axially relative to the cannula to expose the filter and allow the filter to expand and engage the wall of the vessel.

According to more detailed aspects, the method may further comprise the step of manipulating the cannula to adjust the relative positions of the centering legs to substantially center the cannula within the vessel. The manipulating step preferably includes axial translation of the cannula, and may also include axial translation of the outer sheath and cannula together to adjust the position of the set of centering legs. The cannula may also be rotated to adjust the position of the set of centering legs. The step of translating the control wire includes the step of manipulating the control wire to actuate the release mechanism and disengage the filter.

When the filter has been deployed, the method may further comprise the step of translating the control wire axially relative to the cannula to position the control wire inside the cannula. The step of translating the cannula axially relative to the outer sheath to position the cannula inside the outer sheath may also be performed. Finally, the method includes the step of moving the self centering delivery catheter from the vessel.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 3 is a side view similar to FIGS. 1 and 2, showing the deployment of the filter;

FIG. 4 is a side view, partially cut-away and partially in section, of another embodiment of a self centering delivery catheter constructed in accordance with the teachings of the present invention;

FIG. 5 is a side view similar to FIG. 4, showing the centering legs and extended in an extended position;

FIG. 6 is a side view similar to FIGS. 4 and 5, showing the centering legs in an extended position;

DETAILED DESCRIPTION OF THE INVENTION

Figure 1:
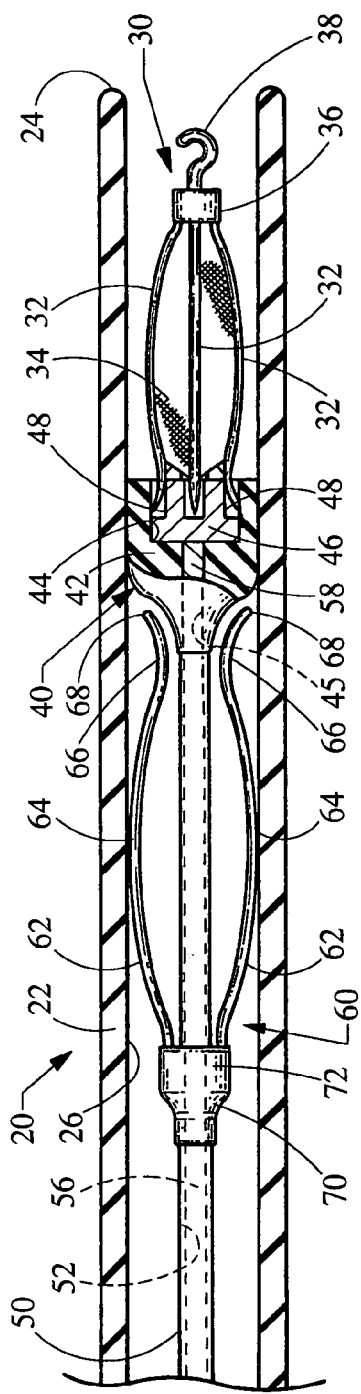
FIG. 1 depicts a side view, partially cut-away and partially in section, of a self centering delivery catheter constructed in accordance with the teachings of the present invention.
Figure 2:
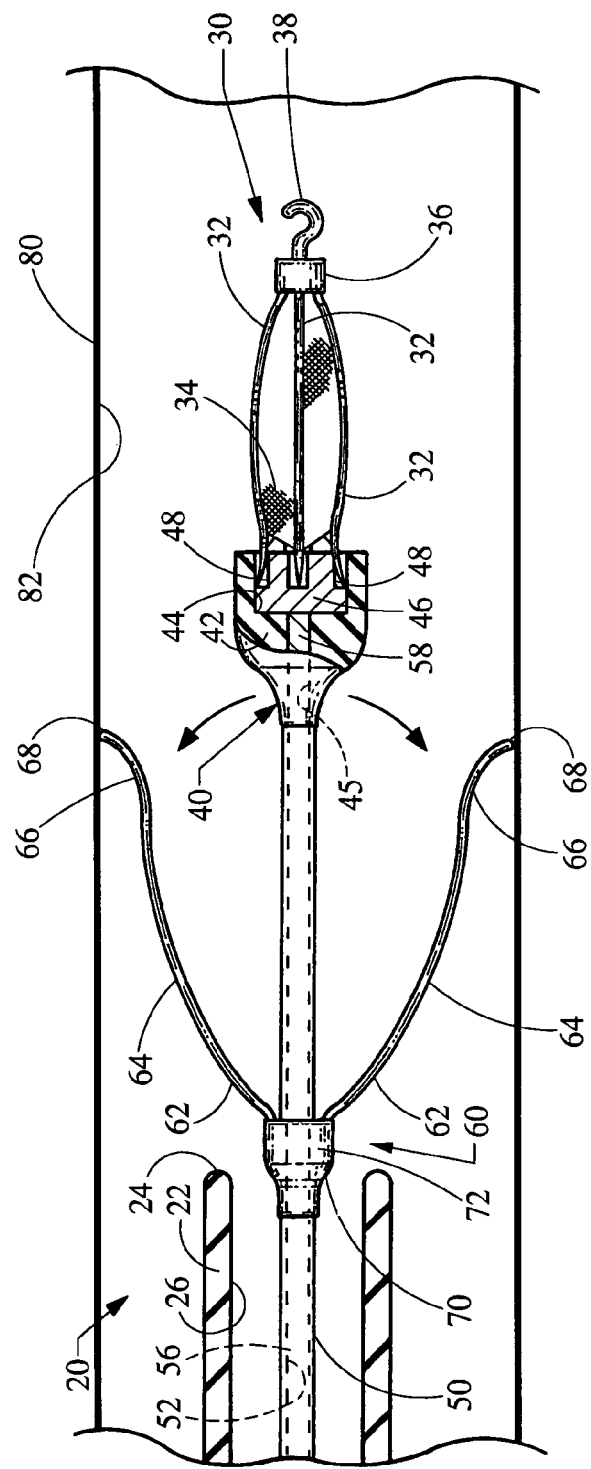
FIG. 2 is a side view similar to FIG. 1, showing the centering legs in an extended position.
Figure 7:
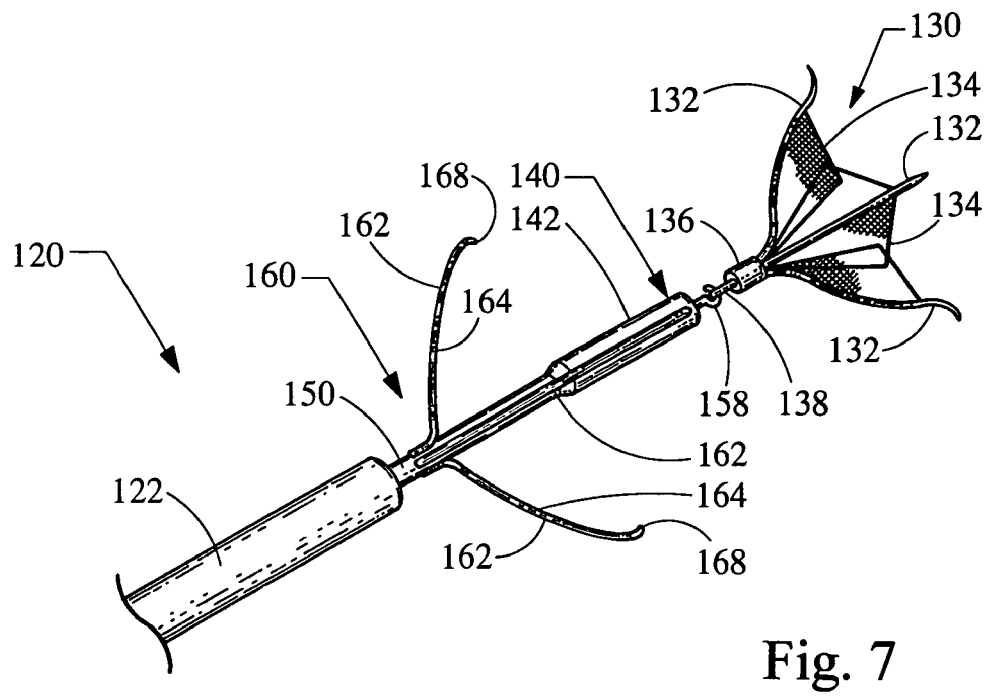
FIG. 7 is a perspective view of the self centering delivery catheter depicted in FIG. 4–6.

Turning now to the figures, FIG. 1 depicts a side view, partially cut-away and partially in section, of a self centering delivery catheter 20. The delivery catheter 20 is employed to deliver a filter 30 into a vessel 80 (FIG. 2). The delivery catheter 20 generally comprises an outer sheath 22 having a distal end 24 and defining a lumen 26. The lumen 26 is sized to receive the filter 30 in its undeployed state, shown in FIG. 1. The filter 30 generally includes a set of struts 32 which are interconnected by a filter medium 34. One end of each of the struts 32 is connected to a central hub 36, which includes a retrieval hook 38 projecting away therefrom. The filter 30 is retained inside the catheter lumen 26 by a release mechanism 40 for eventual deployment, as will be described in further detail herein. While the illustrated embodiments of the present invention will be described with a filter 30, it will be recognized that the present invention is suitable for use with numerable types of expandable intraluminal devices such as stents or valves, as well as different filter types which may or may not have a filtering medium 34. The release mechanism 40 can be readily replaced or adapted to maintain any expandable intraluminal device in its un-deployed state (i.e. retracted or collapsed) prior to delivery.

A cannula 50 is disposed inside the outer sheath 22, and in particular inside the lumen 26. The cannula 50 is preferably made of a flexible material such as plastic or rubber, as is known in the art. The cannula 50 defines a cannula lumen 52, which is sized to receive a control wire 56. The cannula 50 is axially translatable relative to the outer sheath 22, while the control wire 56 is axially translatable relative to the cannula 50.

A set of centering legs 60 are attached to cannula, and in particular are attached to the outer periphery of the cannula 50. As shown in the figures, a cap 70 circumscribes the cannula 50 and includes an increased diameter portion 72 which receives the set of center legs 60. The set of centering legs 60 generally include a plurality of legs 62, which preferably number between three and six legs. Each centering leg 62 may be soldered into the cap 70 around the cannula 50. It will be recognized that the centering legs 60 may be attached in any suitable fashion such as by welding techniques including laser welding and ultrasonic welding, or alternatively may be glued or otherwise attached with an adhesive. A retention structure can also be formed between the cap 70 and the centering legs 60 which provide a mechanical engagement or friction fit to attach the set of centering legs 60 to the cannula 50.

Each leg includes a first curvature 64 which has its concavity facing radially inward towards the cannula 50. Each centering leg 62 also preferably includes a second curvature 66 which has its concavity facing radially outward away from the flexible cannula 50. Each of the centering legs 62 includes a tip portion 68 which ultimately engages the vessel 80. Each distal tip 68 is preferably atraumatic, that is they have no sharp corners, edges, points or the like. Similarly, the distal tip 68 could include a coating or other material which protects against damage to the vessel 80. The set of centering legs 60 are preferably constructed of a memory material such as a superelastic alloy (e.g. nitinol) or stainless steel. However, each centering leg 62 may be constructed of any material which allows the centering leg to be biased radially outwardly away from the cannula 50. As such, the set of centering legs 60 press against the outer lumen 26 as shown in FIG. 1.

The free ends 68 of the set of centering legs 60 curve radially outwardly and overlap a second cap 42 formed at the distal end of the cannula 50. Stated another way, the distal end of the cannula 50 defines a cap 42 which forms a portion of the release mechanism 40. In particular, the cap 42 defines a bore 44 which is sized to receive a cylinder 46. The cylinder 46 includes a series of channels 48 which receive the free ends of the struts 32 of the filter 30. As shown in FIG. 1, the struts 32 are engaged by the release mechanism 40 by virtue of being positioned between the cap 42 and the cylinder 46 within the channels 48. The control wire 56 extends through the cannula 50 and the cap 42 and engages the cylinder 46 at the wires' distal end 58 for deploying the filter 30 as will now be described with references to FIGS. 2 and 3.

With reference to FIG. 2, the delivery catheter 20 is positioned inside the vessel 80 defined by a vessel wall 82. The distal end 24 of the outer sheath 22 is positioned proximate a location within the vessel 80 where deployment of the filter 30 is desired. The outer sheath 22 is translated axially relative to the cannula 50, and is moved to the left (bottom of the page) in FIGS. 1 and 2. In this way, the set of centering legs 60 are positioned outside the outer sheath 22. As previously described, each centering leg 62 is biased radially outwardly, and therefore moves away from the central axis of the cannula 50 as indicated by the arrows in FIG. 2. Ideally, each of the centering legs 62 moves about an equal distance or angle such that the delivery catheter 20, and in particular the cannula 50 and control wire 56 are centered within the vessel 80. Once the centering legs 60 have engaged the vessel wall 82, the cannula 50, and preferably the cannula 50 and sheath 22 together, may be manipulated in order to properly center the catheter 20 within the vessel 80. For example, the cannula 50 may be axially translated, and may also be rotated, in order to center the catheter 20 as well as possible within the vessel 80.

Turning now to FIG. 3, the control wire 56 is translated axially relative to the cannula 50 (to the right or top of the page in FIG. 3) such that the cylinder 46 is moved at least partially outside the bore 44 defined by the cap 42. In this way, the channels 48 formerly containing the filter struts 32 are exposed to the vessel 80, freeing the free ends of the struts 32 and allowing the filter 30 to expand to its deployed state, as indicated by the arrows shown in FIG. 3. In this way, the filter 30 is substantially centered within the vessel 80, providing for easier retrieval of the filter 30 at a future point in time.

The final steps of the method include axially translating the control wire to return the cylinder 46 to a position within the cap 42. The outer sheath 22 is then translated axially relative to the cannula 50 in order to position the set of centering legs 60 inside the outer lumen 26 of the outer sheath 22. It will be noted that the curvatures 64, 66 of each centering leg 62 assists with the return of the leg 62 to its position extending along the cannula 50. Once the set of centering legs 60 and the release mechanism 40 are again positioned inside the outer sheath 22, the entire delivery catheter 20 may be removed from the vessel 80.

Another embodiment of a self centering delivery catheter 120 is depicted in FIGS. 4–7. This embodiment is similar in design and use to the embodiment of FIGS. 1–3, and thus the differences between the two embodiments will be discussed. It can be seen that the cap 170, and in particular its increased diameter portion 172 has an outer diameter approximately equal to or slightly less than the diameter of the lumen 126. In this way, the position of the cannula 150 is more closely tied to the position of the outer sheath 122 when the set of centering legs 160 are deployed.

A set of centering legs 160 are attached to the cannula 150 by way of the hub 170, as discussed with reference to the prior embodiment. It will be recognized that each centering leg 162 is of a shape which has a single curvature 164, the concavity of which is facing radially inward towards the cannula 150. In this way, the distal tip portion 168 of each centering leg 162 is curving radially inwardly towards the cannula 150, making the tip portion 168 very atraumatic. As in the prior embodiments, the distal tips 168 of each centering leg 162 may be designed atraumatically in additional manners.

The release mechanism 140 is substantially different from the prior release mechanism 40. In particular, the cannula 150 includes a distal end portion 142 of increased diameter, and in particular the cannula 150 and its lumen 144. is increased in size in order to receive the filter 130. It can also be seen that the filter 130 has been rotated 180° such that the retrieval hook 138 is facing proximally. The control wire 156 includes a delivery hook 158 at its distal end. The hook 158 is structured to engage the retrieval hook 138 and hub 136 of the filter 130.

As shown in FIG. 5, the sheath 122 may be translated axially (to the left or bottom of the page in FIGS. 5 and 6) relative to the cannula 150 in order to expose the set of centering legs 160 which move radially outwardly to engage the wall 182 of the vessel 180. At the same time, the enlarged distal end 142 of the cannula 150 is exposed to the vessel 180. Thus, the cannula 150 may be axially translated relative to the control wire 156, such that the filter 130 is positioned outside of the distal portion 142 of the cannula 150. The atraumatic design of the tip portion 168 of the centering legs 160 allows the cannula 150 to move relative to the vessel 180 without damage to the vessel 180. Alternatively, the control wire 156 may be translated axially relative to the cannula 150 such that the delivery hook 158 presses against the retrieval hook 138 and/or hub 136 to position the filter 130 outside of the distal portion 142 of the cannula 150. As in the prior embodiment, the filter 130 is allowed to expand to its deployed state whereby the struts 134 engage the wall 182 of the vessel 180. The control wire 156 may be then be manipulated, and in particular twisted or rotated to disengage the hook 158 from the retrieval hook 138 and hub 136 of the filter 130. The entire delivery catheter 120 may then be removed from the vessel 180, as in the previous embodiment.

Figure 8:
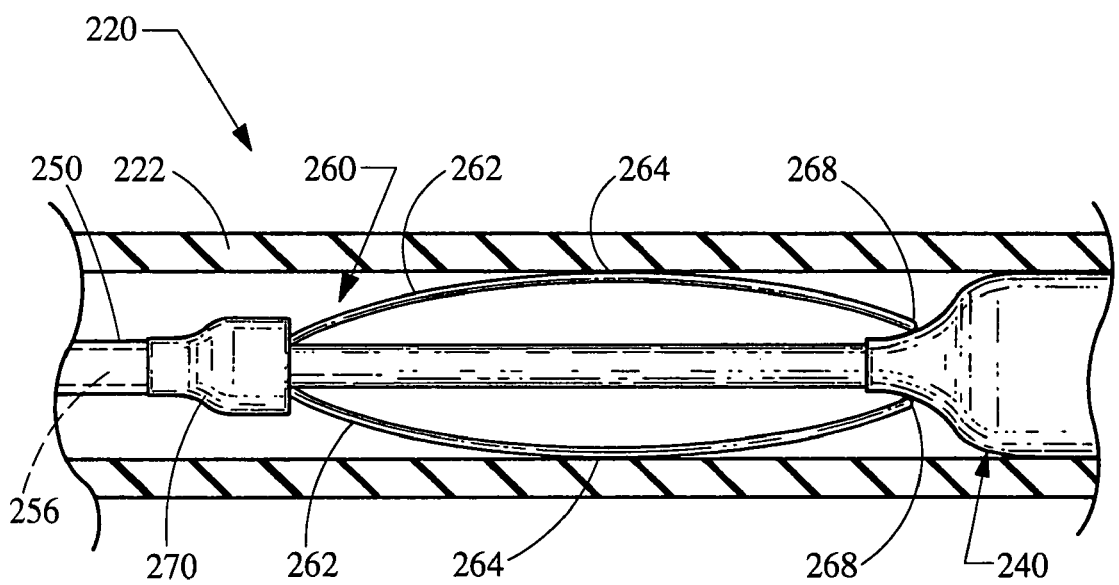
FIG. 8 is a side view, partially cut-away and partially in section, of an embodiment of the self centering delivery catheter similar to the embodiment of FIG. 1–3 but showing a different set of centering legs.

Another embodiment of the self centering delivery catheter 220 has been depicted in FIG. 8. This embodiment is substantially similar in all respects to the embodiment depicted in FIGS. 1–3, and thus the details will not be recited here for the sake of brevity. The outer sheath 222 is sized to receive a cannula 250 having a control wire 256 situated therein. A release mechanism 240 is provided for deployment of the filter. A set of centering legs 260 are attached to the cannula 250 by way of the hub 270, as discussed with reference to the prior embodiments. It will be recognized that each centering leg 262 is of a shape similar to that of the embodiment depicted in FIGS. 4–7. Namely, each let 262 has a single curvature 264, the concavity of which is facing radially inward towards the cannula 250. In this way, the distal tip portion 268 of each centering leg 262 is curving radially inwardly towards the cannula 250, making the tip portion 268 very atraumatic. As in the prior embodiments, the distal tips 268 of each centering leg 262 may be designed atraumatically in additional manners.

Figure 9:
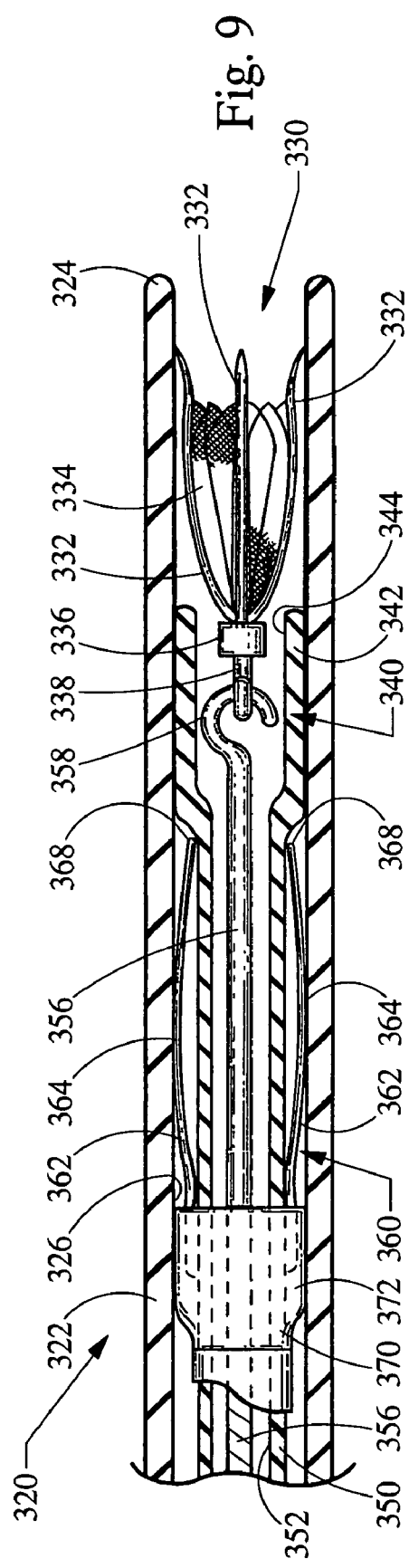
FIG. 9 is a side view, partially cut-away and partially in section, of another embodiment of a self centering delivery catheter constructed in accordance with the teachings of the present invention.

Yet another embodiment of the self centering delivery catheter 320 has been depicted in FIG. 9. This embodiment is substantially similar to the embodiment depicted in FIGS. 4–7, and thus the details will not be restated here for the sake of brevity. The delivery catheter 320 is depicted in an un-deployed state in FIG. 8, where a filter 330 is positioned inside of a cannula 350, which in turn is positioned inside of an outer sheath 322. The set of centering legs 360 are of a design similar to that of FIGS. 1–3, wherein each centering let 362 includes two curvatures 364, 366 and a distal tip portion 368 which curves radially outwardly and is atraumatic.

Similar to the prior embodiments, the release mechanism 340 includes an enlarged portion 342 of the cannula 350 that receives a delivery hook 358 of the control wire 356. The delivery hook 358 works with the retrieval hook 338 and hub 336 of the filter 330. Unlike the prior embodiments, the enlarged portion 342 of the cannula 350 does not contain the filter 330, and in particular is does not restrain the struts 332 of the filter 330. Rather, the outer sheath 322 itself contains the filter struts 332 within its lumen 326. In operation, the outer sheath 322 is translated axially relative to the cannula 350, thereby freeing the filter 320 and allowing the struts 332 to expand to the filter's deployed position. It will be noted that in this embodiment, the filter is thus deployed prior to the deployment of the centering legs 360, and thus the filter 330 may be offset or skewed from the central axis of the vessel (80, 180 in FIGS. 3, 6).

Before the control wire 356 is manipulated to release the filter 320, the outer sheath 320 is further translated axially relative to the cannula 350 to release the centering legs 360, as in the prior embodiments. When the centering legs 360 are deployed, the control wire 356 and hook 358 are substantially centered within the vessel, thereby centering the hub 336 and hook 338 of the filter 330 within the vessel. If desired, the control wire 356 may be manipulated further to ensure the filter 330 is substantially centered within the vessel. The control wire 356 may be then be manipulated, and in particular twisted or rotated to disengage the hook 358 from the retrieval hook 338 and hub 336 of the filter 330.

Figure 10:
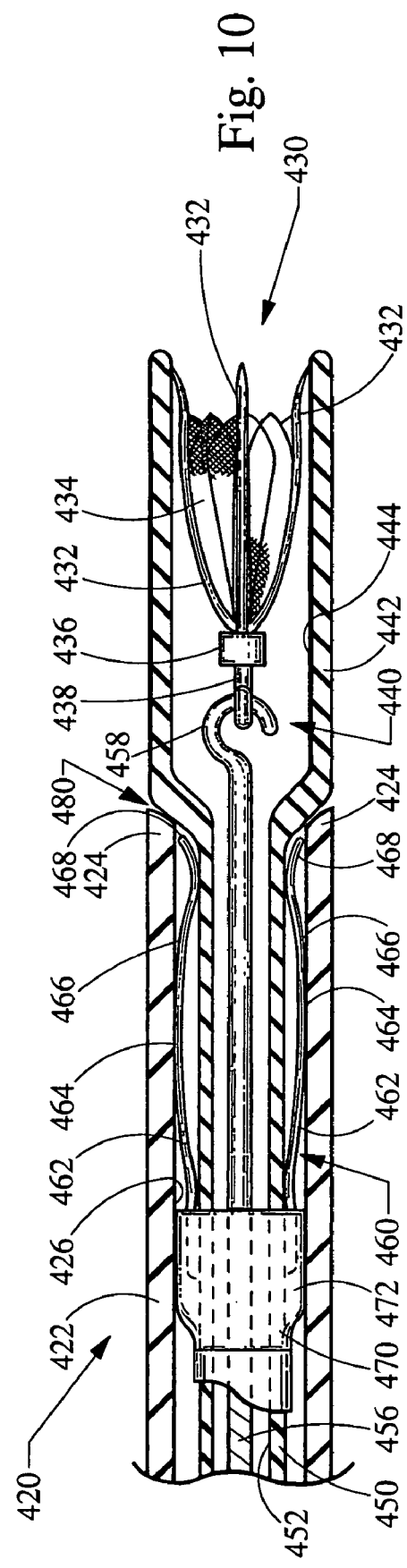
FIG. 10 is a side view, partially cut-away and partially in section, of yet another embodiment of a self centering delivery catheter constructed in accordance with the teachings of the present invention.

Still yet another embodiment of the self centering delivery catheter 420 has been depicted in FIG. 10. This embodiment is substantially similar to the embodiment depicted in FIGS. 4–7, and thus the details will not be restated here for the sake of brevity. The delivery catheter 420 is depicted in an un-deployed state in FIG. 10, where a filter 430 is positioned inside of a cannula 450, which in turn is positioned inside of an outer sheath 422. The set of centering legs 360 are of a design similar to that of FIGS. 1–3, wherein each centering leg 362 includes two curvatures 364, 366 and a distal tip portion 368 which curves radially outwardly and is atraumatic.

Similar to the prior embodiment, the cannula 450 includes an enlarged portion 442 at its distal tip region 344. The enlarged portion 442 also houses the filter 430 in its un-deployed state. Unlike the prior embodiment, the outer sheath 422 has a distal tip 424 which ends at a location distal of the centering legs 460, and in particular the distal tips 468 of each leg 462. At this same location, the cannula 450 transitions to the enlarged portion 442, which has an outer diameter substantially equal to the outer diameter of the outer sheath 422. In this way, the outer sheath 422 and the enlarged portion 442 of the cannula 450 define a smooth transition area 480 that allows the device 420 to be passed through the vascular system in the same manner a single elongated tube or catheter is passed and positioned within a vessel.

In operation, once the device 420 has been positioned in the target area of the vessel, the outer sheath 422 may be translated axially relative to the cannula 450 to expose the set of centering legs 460 and allow them to expand or move radially outwardly to engage the vessel. With the device 420 centered, the filter 430 may then be deployed. At the same time, the enlarged distal end 442 of the cannula 450 remains exposed to the vessel. Thus, the cannula 450 may be axially translated relative to the control wire 456, such that the filter 430 is positioned outside of the distal portion 442 of the cannula 450. The atraumatic design of the tip portion 468 of the centering legs 460 allows the cannula 450 to move relative to the vessel without damage thereto. Alternatively, the control wire 456 may be translated axially relative to the cannula 450 such that the delivery hook 458 presses against the retrieval hook 438 and/or hub 436 to position the filter 430 outside of the distal portion 442 of the cannula 450. As in the prior embodiment, the filter 430 is allowed to expand to its deployed state whereby the struts 434 engage the wall 482 of the vessel 480. The control wire 456 may be then be manipulated, and in particular twisted or rotated to disengage the hook 458 from the retrieval hook 438 and hub 436 of the filter 430. The entire delivery catheter 420 may then be removed from the vessel, as in the previous embodiments.

Accordingly, the present invention provides a self centering delivery catheter which greatly improves the accuracy with which a retrieval device such as a filter may be deployed in a vessel. The unique design and method of the present invention allows a cannula having a control wire and a release mechanism to be substantially centered within the vessel prior to deployment of the filter. The invention also allows for adjustment of the set of centering legs to best center the cannula and release mechanism for centered deployment of the filter. It will be recognized that numerous modifications may exist, including modifications on the centering mechanism. For example, a second cannula with distal slits could be disposed around the existing cannula, the relative movement of the two cannulas cooperating to expand centering wings to substantially center the release mechanism within the vessel. Such devices are generally known as a Malecot-type catheter. Additional means for centering the device can replace the expandable centering legs, such as expandable wire baskets or balloons. Such centering mechanisms are well known and also described in co-pending U.S. patent application Ser. No. 10/804,386, filed on Mar. 19, 2004, which claims priority to Provisional Application No. 60/455,914 filed Mar. 19, 2003, the disclosures of which are hereby incorporated by reference in their entirety.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled The invention claim is:

1. A self centering delivery catheter for delivery of an expandable intraluminal device into a vessel, the delivery catheter comprising:
   an outer sheath;
   a cannula disposed inside the outer sheath and axially translatable relative to the outer sheath;
   a set of centering legs attached to the cannula, the centering legs being operable between a first retracted position and a second extended position, the centering legs moving radially away from the cannula as the centering legs move from the first position to the second position;
   the relative position of the outer sheath and cannula controlling operation of the centering legs between the first and second positions;
   a control wire disposed inside the cannula and axially translatable relative to the cannula; and
   a release mechanism formed near a distal end of the control wire, the release mechanism structured to engage and disengage the expandable intraluminal device, the release mechanism including a cap formed at a distal end of the cannula, the cap including a bore receiving a cylinder, the cylinder operatively connected to a the control wire, the cap including channels receiving struts of the expandable intraluminal device, the cap and cylinder cooperating to engage the expandable intraluminal device, axial translation of the control wire operating the release mechanism to disengage the expandable intraluminal device.

2. The delivery catheter of claim 1, wherein the centering legs are biased towards the second extended position.

3. The delivery catheter of claim 1, wherein the centering legs are positioned inside the outer sheath in the first retracted position, and wherein the centering legs are positioned outside the outer sheath in the second extended position.

4. The delivery catheter of claim 1, wherein the centering legs are constructed of a memory material.

5. The delivery catheter of claim 1, wherein the free end of each centering leg is atraumatic.

6. The delivery catheter of claim 1, wherein each centering leg has a concave curvature facing the cannula.

7. The delivery catheter of claim 6, wherein each centering leg includes a first end attached to the cannula and a second free end, the second free end having a curvature extending radially away from the cannula.

8. The delivery catheter of claim 1, further comprising a hub circumscribing the cannula, the hub connecting the set of centering legs to the cannula.

9. The delivery catheter of claim 1, wherein a distal end of the cannula receives the expandable intraluminal device, and wherein axial translation of the cannula relative to the control wire places the expandable intraluminal device outside of the cannula.

10. The delivery catheter of claim 9, wherein the cannula includes an increased diameter portion sized to receive the expandable intraluminal device and hook.

11. The delivery catheter of claim 1, wherein axial translation of the control wire positions the cylinder relative to the cap to disengage the expandable intraluminal device.

\* \* \* \* \*